United States Patent [19]

Yoneda

[11] Patent Number: 4,573,360
[45] Date of Patent: Mar. 4, 1986

[54] BENDING TEST APPARATUS

[75] Inventor: Akiyoshi Yoneda, Akashi, Japan

[73] Assignee: Amada Company, Limited, Japan

[21] Appl. No.: 586,038

[22] Filed: Mar. 5, 1984

[30] Foreign Application Priority Data

Mar. 4, 1983 [JP] Japan .............................. 58-30401[U]

[51] Int. Cl.⁴ .............................................. G01N 3/20
[52] U.S. Cl. ........................................... 73/850; 73/852
[58] Field of Search ................. 73/849, 850, 851, 852, 73/853, 854

[56] References Cited

U.S. PATENT DOCUMENTS 3,057,191 10/1962 Holloway .............................. 73/849

Primary Examiner—Jerry W. Myracle
Attorney, Agent, or Firm—Wigman & Cohen

[57] ABSTRACT

The present invention relates to a bending test apparatus comprising a first bending device mounted on a vertically slidable rack. Test piece gripping means are mounted on arms attached to sector gears arranged such that when the first bending device and the rack are moved vertically downward toward the test piece, the rack engages with the sector gears so as to upwardly and inwardly swing the gripping devices. A pair of slidable devices for further bending the test piece are arranged on opposite sides of the first testing device and are adapted to converge on the test piece to further bend it after it has been previously bent by the first bending device.

15 Claims, 4 Drawing Figures

BENDING TEST APPARATUS

BACKGROUND OF THE INVENTION

1. Field of the Invention

The present invention relates to a bending test apparatus for making a bending test on an elongated material or strip such as a bandsaw blade which has been welded into an endless shape. More particularly, the present invention pertains to a bending test apparatus for testing the bending strength of an elongated material such as a bandsaw blade by bending such a material.

2. Description of the Prior Art

It is often necessary to make a bending test on an elongated material or strip such as a bandsaw blade by bending such a material to test the strength of the same. Since bandsaw blades are welded into an endless shape or loop by welding ends of each bandsaw blade by means of a welding machine, a bending test is necessary to test the strength of a welded portion of a bandsaw blade to see the welding condition.

Heretofore, in order to see, for example, the welding condition for welding bandsaw blade into endless shapes, it has been customary to manually bend the welded portion of a bandsaw blade which has been welded to see the bending strength of the same from experience. Therefore, it has been inconvenient that the strength of the bandsaw blade allowable is swayed by the skill and experience of those who perform such tests, and it has been impossible to make an accurate bending test in this manner.

As an improved conventional manner, a bending test is performed by making a test ring having a radius of curvature and by manually pressing a test piece of elongated materials into such a curvature to see whether or not the test piece is broken. In this manner, however, it is necessary and troublesome to make many test rings for a variety of thicknesses and widths of elongated materials such as bandsaw blades. Furthermore, it is impossible in this manner to make an accurate bending test to see at what degree of bending the elongated material to be tested is broken.

SUMMARY OF THE INVENTION

It is an object of the present invention to provide a bending test apparatus by which an accurate bending test can be made on an elongated material such a bandsaw blade to see the bending strength of the same.

It is another object of the present invention to provide a bending test apparatus by which a bending test can be easily made on an elongated material such as a bandsaw blade without special means to see the bending strength of the same.

In order to attain these objects, the bending apparatus according to the present invention is provided with a first bending means and a pair of second bending means which are all movable by power to bend a test piece of an elongated material. The first bending means is vertically movable to primarily bend the test piece to a degree, and the second bending means are horizontally movable to further bend the test piece which has been bent by the first bending means. The first and second bending means are so arranged that their strokes can be adjusted to adjust the bending degree of the test piece.

Other and further objects and advantages of the present invention will be apparent from the following description and accompanying drawings which, by way of illustration, show a preferred embodiment of the present invention and the principle thereof.

DESCRIPTION OF THE PREFERRED EMBODIMENT

Figure 1:
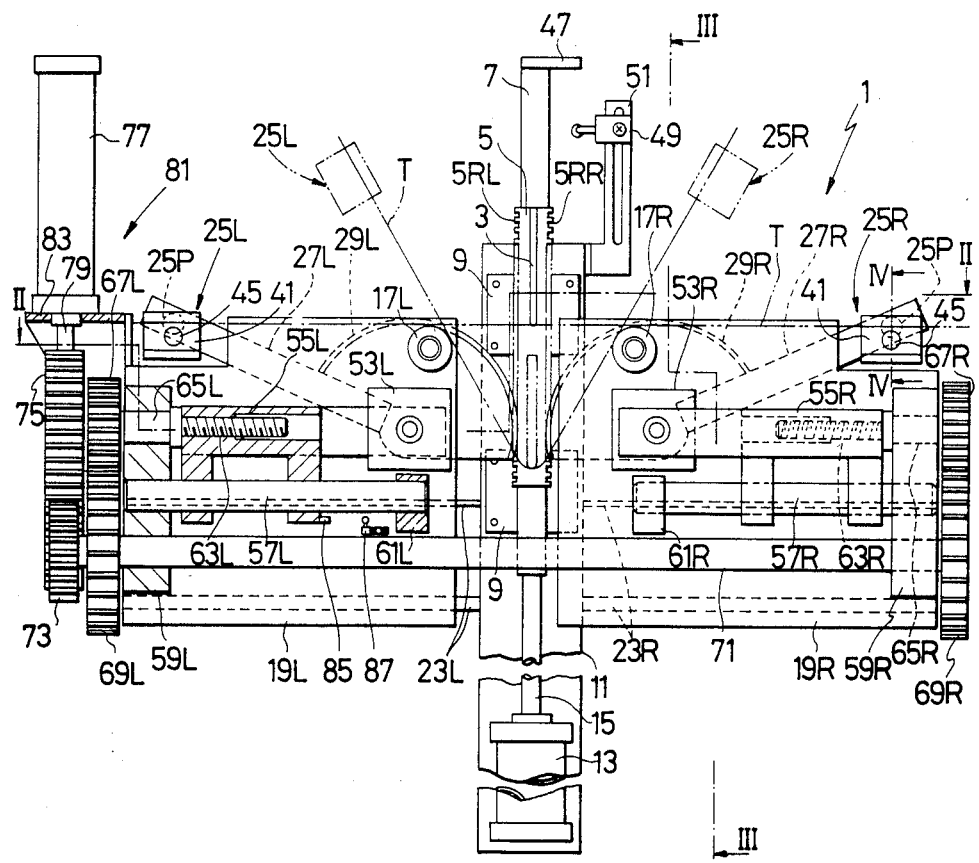
FIG. 1 is a front elevational view of a bending test apparatus according to the present invention in which only major portions are shown.
Figure 2:
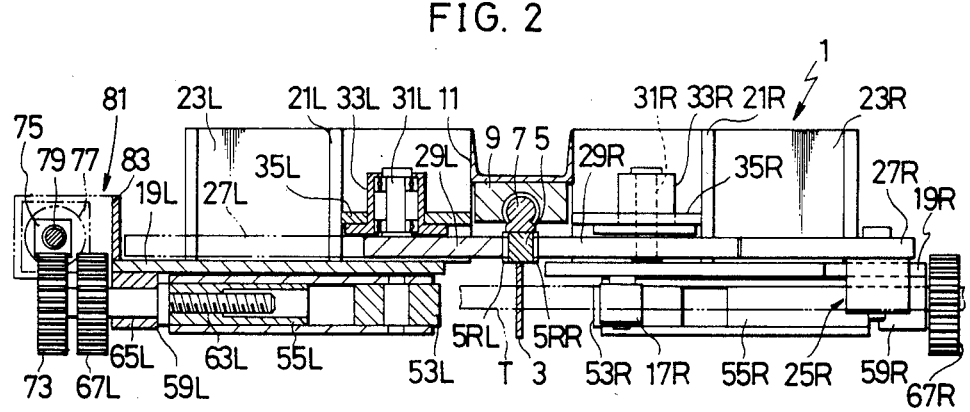
FIG. 2 is a sectional view taken along the line II—II of FIG. 1.

Referring to FIGS. 1 and 2, there is shown a bending test apparatus 1 to make a bending test on a test piece T to which a portion to be tested has been cut from an elongated material or strip such as a bandsaw blade. As will be described in great detail hereinafter, the test piece T is initially horizontally clamped in the bending test apparatus 1 and then bent in the bending test.

Figure 3:
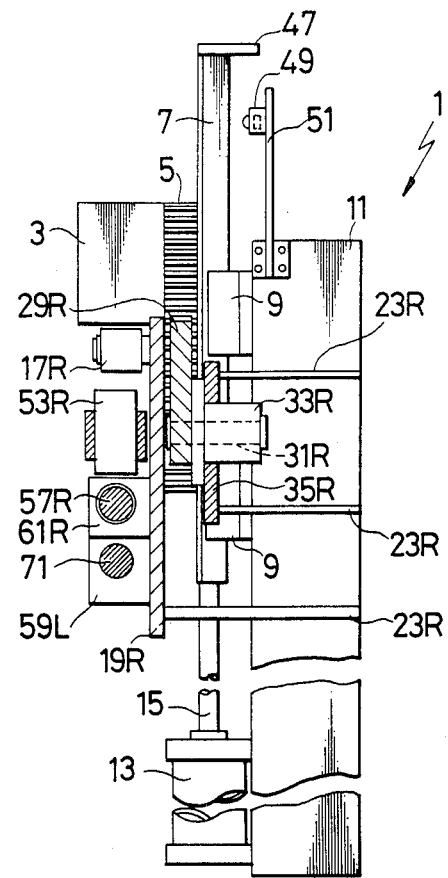
FIG. 3 is a sectional view taken along the line III—III of FIG. 1.

As shown in FIGS. 1, 2 and 3, the bending test apparatus 1 is provided with a first bending means 3 which is a square blade-like member in the preferred embodiment and is vertically movable to initially bend the test piece T in the bending test. The first bending means 3 is fixed to an elongated vertical rack member 5 which is formed with a pair of racks 5RR and 5RL and is integrally fixed to a vertical slide bar 7. More particularly, the first bending means 3 is fixed to the front face of the rack member 5 in a cantilever manner to project frontward therefrom, and the rack member 5 is fixed to the front face of the slide bar 7 with the first bending means 3 projecting frontward. Also, the racks 5RR and 5RL of the rack member 5 are symmetrically formed on the opposite sides of thereof for a purpose which will be described in great detail hereinafter. The slide bar 7 is vertically slidably mounted on a plurality of guide blocks 9 in a manner such that the rack member 5 will project frontward therefrom with the first bending means 3 projecting frontward. The guide blocks 9 are fixed to a post 11 which is vertically fixed at a central rear portion of the bending test apparatus 1 so that the slide bar 7 may be vertically moved therealong together with the first bending means 3. Also, in order to move the slide bar 7, a hydraulic or pneumatic motor 13 is mounted on a lower portion of the post 11 with its piston rod 15 connected with the lower end of the slide bar 7. Thus, it will be understood that the first bending means 3 will be vertically moved by the slide bar 7 when the piston rod 15 of the hydraulic or pneumatic motor 13 is put in motion.

In order to hold the test piece T, a pair of holding rollers 17R and 17L are symmetrically provided on a level with each other below the first bending means 3 on the opposite sides of the course where the first bending means 3 is vertically moved. The holding rollers 17R and 17L are rotatably mounted with their axes horizontal on vertical plates 19R and 19L, respectively, which are provided symmetrically on the opposite sides of the course of the vertical movement of the first bending means 3. The vertical plates 19R and 19L are vertically fixed by means of a plurality of ribs 21R and 21L to a plurality of stay plates 23R and 23L which are horizontally fixed to the post 11 in such a manner as to symmetrically extend horizontally in opposite sideward directions therefrom. Thus, the test piece T is horizontally placed on the holding rollers 17R and 17L beneath the first bending means 3 in the bending test and then is bent thereon to a degree by the first bending means 3 lowered by the hydraulic or pneumatic motor 13 as shown by the imaginary lines in FIG. 1. Also, it will be understood that the test piece T will be moved downwardly on the holding rollers 17R and 17L with its ends swung upwardly inwardly when it is being bent by the first bending means 3.

In order to clamp the test piece T in the bending test, a pair of gripping means 25R and 25L are symmetrically provided on a level with each other on the outside portions of the holding rollers 17R and 17L, respectively. The gripping means 25R and 25L are held on upper ends of a pair of arms 27R and 27L, respectively, which are fixed to a pair of sector gears 29R and 29L, respectively, having shafts 31R and 31L, respectively. As will be described in great detail hereinafter, the gripping means 25R and 25L are pivotally held on the arms 27R and 27L, respectively, and are so designed as to loosely grip the test piece T so that is may be slid therein when being bent. The arms 27R and 27L are fixed aslant to the sector gears 29R and 29L, respectively, in such a manner as to extend outwardly upwardly in radial directions from the axes of the sector gears 29R and 29L, respectively. The sector gears 29R and 29L are rotatably provided symmetrically in engagement with the racks 5RR and 5RL, respectively, of the rack member 5 on the back side of the vertical plates 19R and 19L, respectively. The shafts 31R and 31L of the sector gears 29R and 29L are journaled in bearing assemblies 33R and 33L which are mounted on the stay plates 23R and 23L, respectively, by means of brackets 35R and 35L, respectively. Thus, the sector gears 29R and 29L will be rotated by the racks 5RR and 5RL of the rack member 5 to swing the gripping means 25R and 25L upwardly inwardly when the slide bar 7 is lowered together with the rack member 5. In this connection, the gripping means 25R and 25L are so arranged as to be located on a level with the holding rollers 17R and 17L to clamp the test piece T placed on the holding rollers 17R and 17L when the slide bar 7 and the rack member 5 are at their uppermost position. In this arrangement, the gripping means 25R and 25L will be swung upwardly inwardly by the sector gears 29R and 29L when the first bending means 3 is lowered by the slide bar 7 to bend the test piece T. Accordingly, it will be understood that the gripping means 25R and 25L will follow the ends of the test piece T as shown by imaginary lines in FIG. 1 when the first bending means 3 is bending the test piece T.

Figure 4:
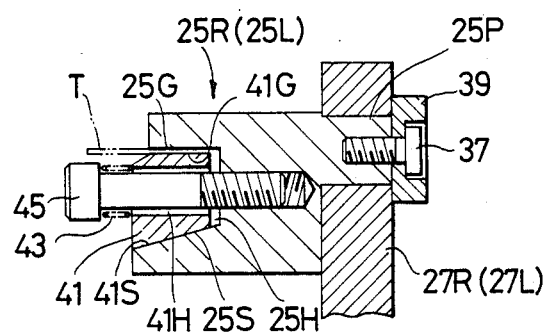
FIG. 4 is a sectional view taken along the line IV—IV of FIG. 1.

Referring to FIG. 4, each of the gripping means 25R and 25L is formed with a pin-like portion 25P and is pivotally held on the arms 27R and 27L by means of the pin-like portion 25P so that it may be swung on an axis which is in parallel with the axes of the holding rollers 17R and 17L. The pin-like portion 25P of the gripping means 25R and 25L is pivotally secured to the arms 27R and 27L by a bolt 37 by means of a collar 39 with its pivoting axes in parallel with the axes of the holding rollers 17R and 17L. Thus, it will be understood that the gripping means 25R and 25L will be swung on the arms 27R and 27L when the ends of the test piece T are swung upwardly inwardly as the test piece T is bent by the first bending means 3.

Referring further to FIG. 4, each of the gripping means 25R and 25L is formed with a hole 25H where the test piece T is placed to be gripped in a manner such that it may be moved when being bent by the first bending means 3. The hole 25H of the gripping means 25R and 25L is provided with an upper gripping surface 25G and a lower slope 25S descending outwardly. There is inserted in the hole 25H a gripping member 41 which is provided with an upper gripping surface 41G and a lower slope 41S and is formed at its central portion with a slot-like hole 41H. The gripping member 41 is inserted in the hole 25H with its slope 41S in sliding engagement with the slope 25S in a manner such that the gripping surface 41G may grip the test piece T in cooperation with the gripping surface 25G. Also, the gripping member 41 is resiliently and adjustably secured in the hole 25H by a spring 43 and a bolt 45 which is adjustably threaded through the slot-like hole 41H in the gripping means 25. The arrangement is such that the gripping member 41 can be slid on the slope 25S to adjust the clearance or gripping force between the gripping surfaces 25G and 41G where the test piece T is gripped when the bolt 45 is adjusted. As will be readily understood, the gripping member 41 can be slid on the slope 25S to adjust the clearance or gripping force between the gripping surfaces 25G and 41G since the bolt 45 is threaded in the gripping means 25R and 25L through the slot-like hole 41H. In this arrangement, the test piece T can be loosely gripped between the gripping surfaces 25G and 41G of the gripping means 25 so as to be slid therein when the clearance or gripping force between the gripping surfaces 25G and 41G has been adjusted. Thus, it will be understood that the test piece T can be slid in the gripping means 25R and 25L when it is being bent by the first bending means 3 as shown by the imaginary lines in FIG. 1.

As shown in FIGS. 1, 3 in order to limit the stroke of the vertical movement of the first bending means 3, a dog member 47 is provided on the slide bar 7, and a sensing means 49 such as a limit switch is disposed on a portion of the bending test apparatus 1. As will be readily understood, the sensing means 49 is so disposed as to be actuated by the dog member 47 when the slide bar 7 is lowered to enable the first bending means 3 to bend the test piece T. Also, of course the sensing means 49 is so arranged as to stop the slide bar 7 and the first bending means 3 from lowering as soon as it is contacted by the dog member 47 which has been lowering. In the preferred embodiment, the sensing means 49 is held on a holding member 51 which is fixed to a portion of the post 11 so that it may be adjusted in position to adjust the stroke of the vertical movement of the first bending means 3.

Referring again to FIGS. 1, 2 and 3, a pair of second bending means 53R and 53L are provided at the central portion of the bending test apparatus 1 to further bend the test piece T which has been primarily bent by the first bending means 3 to a degree as shown by the imaginary lines in FIG. 1. The second bending means 53R and 53L are symmetrically disposed on a level with each other on the opposite sides of the course of the vertical movement of the first bending means 3 so as to be horizontally moved toward and away from the course of the first bending means 3. Also, the second bending means 53R and 53L are fixed to a pair of sliding members 55R and 55L, respectively, which are horizontally movable toward and away from the course of the vertical movement of the first bending means 3. The sliding members 55R and 55L are symmetrically and horizontally slidably held on a pair of guide bars 57R and 57L, respectively, which are symmetrically and horizontally fixedly mounted on a pair of brackets 59R and 59L, respectively, and another pair of brackets 61R and 61L, respectively. The brackets 59R and 59L are symmetrically fixed to the outer ends of the vertical plates 19L and 19R, respectively, while the brackets 61R and 61L are likewise fixed to the inner ends of the vertical plates 19R and 19L, respectively.

The second bending means 53R and 55L are so arranged as to be horizontally moved toward and away from the course of the vertical movement of the first bending means 3 by a pair of lead screws 63R and 63L, respectively. The lead screws 63R and 63L are disposed in engagement with the sliding members 55R and 55L, and they are threaded in a reversal relationship with each other so that they may move the sliding members 55R, 55L toward and away from each other when simultaneously rotated in the same direction. Also, the lead screws 63R and 63L are fixed to shafts 65R and 65L, respectively, which are rotatably held on the brackets 59R and 59L, respectively, and are provided with gears 67R and 67L, respectively, at their ends. The gears 67R and 67L are symmetrically disposed at outer portions of the bending test apparatus 1 in engagement with a pair of gears 69R and 69L, respectively, which are coaxially fixed to an elongated shaft 71 so as to be simultaneously driven. The shaft 71 is horizontally and rotatably held on the brackets 59L and 59R and is provided with a pinion gear 73 which is disposed in engagement with a rack member 75 in the preferred embodiment. Also, in order to drive the rack member 75, there is provided hydraulic or pneumatic motor 77 which has a piston rod 79 connected to the rack member 75 and is mounted on a portion 81 of the bending test apparatus 1 by means of a bracket 83. In this arrangement, when the rack member 75 is driven by the motor 77 to rotate the pinion gear 73, the shaft 71 will be rotated by the pinion gear 73 to simultaneously rotate the gear 69R and 69L so as to simultaneously rotate the gears 67R and 67L and the lead screws 63R and 63L. Since the lead screws 63R and 63L have to be threaded in a reversal relationship to each other, they will move the second bending means 53R and 53L by means of the sliding members 55R and 55L toward and away from the course of the vertical movement of the first bending means 3. Thus, it will be understood that, when the motor 77 is put in motion, the second bending means 53R and 53L can be simultaneously moved by the lead screws 63R and 63L to further bend the test piece T which has been primarily bent to a degree by the first bending means 3.

As shown in FIG. 1, in order to limit the stroke of the second bending means 53R and 53L, a dog member 85 is provided on either of the sliding members 55R and 55L, and a sensing means 87 such as a limit switch is provided on a portion of the bending test apparatus 1. The sensing means 87 is so disposed that it is contacted by the dog member 85 when the second bending means 53R and 53L are moved by the sliding members 55R and 55L to bend the test piece T. Of course, the sensing means 87 is so arranged as to stop the motor 77 to stop the second bending means 53R and 53L as soon as it is contacted by the dog member 85. Also, the sensing means 87 is so disposed as to be adjusted in position to adjust the stroke of the second bending means 53R and 53L with a view to adjusting the angle to which the test piece T is to be bent by the second bending means 53R and 53L. Thus, when second bending means 53R and 53L are stopped from moving, the bending degree of the test piece T can be taken according to the position of the sensing means 87. As will be readily understood, a bending test can be made to see the bending strength of the test piece T according to whether or not the test piece T is broken before the second bending means 53R and 53L have been stopped. Also, it will be understood that the stroke of the second bending means 53R and 53L can be adjusted by changing the position of the sensing means 87 to adjust the bending degree according to the width and thickness of the test piece T. In this connection, it is also possible to make a bending test by seeing the load by which the test piece T is broken, if a load sensing means is provided at a portion of the second bending means 53R and 53L where the test piece T is pressed to be bent.

In the above described arrangement, the test piece T will be initially bent by the first bending means 3 to a degree and then will be finally bent by the second bending means 53R and 53L. When the first bending means 3 is bending the test piece T to cause the ends of the same to be swung up, the gripping means 25R and 25L gripping the test piece T will be swung up by the sector gears 29R and 29L to follow the swinging ends of the test piece T. Also, when the first bending means 3 is bending the test piece T, the gripping means 25R and 25L will not only follow the ends of the test piece T but also will keep gripping loosely the test piece T which will be moved downwardly on the holding rollers 17R and 17L. After the first bending means 3 has bent the test piece T to a degree, the second bending means 53R and 53L will be simultaneously horizontally moved to further bend the test piece T which has been downwardly bent so that a bending test may be performed. Also, the stroke of the second bending means 53R and 53L can be adjusted by changing the position of the sensing means 87 to adjust the bending degree according to the width and thickness of the test piece T.

As has been far described in the above, an accurate bending test can be made easily on an elongated material such as a bandsaw blade by use of the bending test apparatus 1 according to the present invention. Since the bending test is mechanically done by the bending test apparatus 1, the bending test or the strength of an elongated material allowable is always accurate and reliable without being swayed by the skill and experience of one who performs the bending test as has been the case heretofore.

Although a preferred form of the present invention has been illustrated and described, it should be understood that the device is capable of modification by one skilled in the art without departing from the principles of the invention. Accordingly, the scope of the invention is to be limited only by the claims appended hereto.

I claim:
1. A bending test apparatus comprising:
   first guide means mounted on the apparatus and extending in a first direction;
   first bending means movable on the first guide means in the first direction to bend a test piece to a degree;
   second guide means mounted on the apparatus and extending in a second direction;
   and a pair of second bending means is movable on the second guide means in the second direction to further bend the test piece which has been bent by the first bending means.
2. The bending test apparatus according to claim 1 in which a stroke adjusting means for adjusting the stroke of the said second bending means is so provided as to be adjusted in position.

3. The bending apparatus according to claim 1, wherein the second bending means comprises left bending means and right bending means movable on the second guide means so as to simultaneously move in opposite directions.

4. The bending apparatus according to claim 3, wherein the left and right bending means are adapted to converge on the previously bent test piece to further bend the workpiece.

5. The bending apparatus according to claim 3, wherein the left and right bending means are adapted to converge on the previously bent test piece to further bend the workpiece.

6. The bending apparatus according to claim 1, further comprising a rack means slidable on the first guide means and the first bending means being mounted on the rack means.

7. The bending apparatus according to claim 6, further comprising:
sector gears engaged with the rack member to rotate as the rack member slides; and
test piece gripping means fixed to the sector gears;
the gripping means mounted so as to swing upward and inward as the first bending means and rack member move toward the test piece.

8. A bending test apparatus, comprising:
first bending means movable provided to bend a test piece to a degree;
a pair of second bending means movably provided to further bend the test piece which has been bent by the first bending means;
the second bending means being movably and symmetrically provided on opposite sides of the course of the movement of the first bending means; and
a driving mechanism is provided to move the second bearing means toward and away from each other.

9. The bending apparatus according to claim 8, wherein the second bending means comprises left bending means and right bending means mounted on the bending test apparatus so as to simultaneously move in opposite directions.

10. The bending apparatus according to claim 9, further comprising rack means slidable on the bending apparatus and the first bending means mounted on the rack means.

11. The bending apparatus according to claim 8, further comprising:
sector gears engaged with the rack member to rotate as the rack member slides; and
test piece gripping means fixed to the sector gears;
the gripping means mounted so as to swing upward and inward as the first bending means and rack member move toward the test piece.

12. A bending test apparatus, comprising:
first bending means movably provided to bend a test piece to a degree;
a pair of second bending means movably provided to further bend the test piece which has been bent by the first bending means;
a pair of gripping means for gripping ends of the test piece rotatably and symmetrically provided on opposite sides of the course of the movement of the first bending means; and
a driving mechanism is provided to rotate the gripping means to follow the bending of the test piece as the first bending means bends the test piece.

13. The bending apparatus according to claim 12, wherein the second bending means comprises left bending means and right bending means mounted on the bending test apparatus so as to simultaneously move in opposite directions.

14. The bending apparatus according to claim 13, wherein the left and right bending means are adapted to converge on the previously bent test piece to further bend the workpiece.

15. The bending aparatus according to claim 12, further comprising rack means slidable on the bending apparatus and the first bending means mounted on the rack means.

* * * * *

UNITED STATES PATENT AND TRADEMARK OFFICE
CERTIFICATE OF CORRECTION

PATENT NO. : 4,573,360
DATED : March 4, 1986
INVENTOR(S) : AKIYOSHI YONEDA

It is certified that error appears in the above-identified patent and that said Letters Patent is hereby corrected as shown below:

IN THE CLAIMS:

Claim 8, column 7, line 29, "movable" should be
--movably--;
column 7, line 38, "bearinc" should be
--bending--.

Claim 15, column 8, line 37, "aparatus" should be
--apparatus--.

Signed and Sealed this

Fifteenth Day of July 1986

[SEAL]

Attest:

DONALD J. QUIGG

Attesting Officer    Commissioner of Patents and Trademarks